US009872732B2

(12) United States Patent
Blair

(10) Patent No.: US 9,872,732 B2
(45) Date of Patent: Jan. 23, 2018

(54) SURGICAL SPONGE DISTRIBUTION SYSTEMS AND METHODS

(71) Applicant: RF Surgical Systems, Inc., Carlsbad, CA (US)

(72) Inventor: William A. Blair, Carlsbad, CA (US)

(73) Assignee: COVIDIEN LP, Mansfield, MA (US)

( * ) Notice: Subject to any disclaimer, the term of this patent is extended or adjusted under 35 U.S.C. 154(b) by 574 days.

(21) Appl. No.: 14/523,089

(22) Filed: Oct. 24, 2014

(65) Prior Publication Data

US 2015/0115121 A1 Apr. 30, 2015

Related U.S. Application Data

(60) Provisional application No. 61/895,034, filed on Oct. 24, 2013.

(51) Int. Cl.
*A61B 19/02* (2006.01)
*A61F 13/44* (2006.01)
(Continued)

(52) U.S. Cl.
CPC ............ *A61B 19/026* (2013.01); *A61B 50/30* (2016.02); *A61F 13/44* (2013.01); *A61B 2090/0804* (2016.02)

(58) Field of Classification Search
CPC .................. A61B 19/026; A61B 50/30; A61B 2090/0804; A61B 2050/375; A61B 50/37;
(Continued)

(56) References Cited

U.S. PATENT DOCUMENTS 3,630,202 A * 12/1971 Small .................... A61F 15/001
206/370
3,941,132 A * 3/1976 Lenaghan ............. A61F 15/001
604/362
(Continued)

FOREIGN PATENT DOCUMENTS

AU 2003249257 A1 2/2004
CN 101460096 A 6/2009
(Continued)

OTHER PUBLICATIONS

Barnes et al., "Method, Apparatus and Article for Detection of Transponder Tagged Objects, for Example During Surgery," U.S. Appl. No. 61/056,787, filed May 28, 2008, 60 pages.
(Continued)

*Primary Examiner* — Tatyana Zalukaeva
*Assistant Examiner* — Gabriella Burnette
(74) *Attorney, Agent, or Firm* — Seed IP Law Group LLP

(57) ABSTRACT

A surgical sponge dispensing system facilitates the accurate counting of surgical sponges used in a medical procedure. An elongated flexible strip of material carries a plurality of surgical sponges, each attached to the elongated flexible strip of material at a respective fixed location. Demarcations on the elongated flexible strip of material can provide an accurate and reliable indication of the number of surgical sponges detached from the elongated flexible strip of material. Additionally, each of the plurality of surgical sponges and the corresponding attachment location of the sponge to the elongated flexible strip of material may carry a unique alphanumeric identifier. Reconciling the alphanumeric identifiers at locations on the elongated flexible strip of material during a medical procedure can provide an accurate and reliable count of the number of surgical sponges used during the procedure.

13 Claims, 6 Drawing Sheets

(51) Int. Cl.
*A61B 50/30* (2016.01)
*A61B 90/00* (2016.01)

(58) Field of Classification Search
CPC .............. A61F 13/44; D10B 2509/02; A61M 2205/60; A61M 2205/6009
USPC ..................... 604/358; 40/662, 675; 283/81
See application file for complete search history.

(56) References Cited

U.S. PATENT DOCUMENTS

| | | |
|---|---|---|
| 4,034,297 A | 7/1977 | Giorgi et al. |
| 4,966,595 A | 10/1990 | Meringola |
| 5,931,824 A | 8/1999 | Stewart et al. |
| 6,026,818 A | 2/2000 | Blair et al. |
| 6,172,608 B1 | 1/2001 | Cole |
| 6,353,406 B1 | 3/2002 | Lanzl et al. |
| 7,227,469 B2 | 6/2007 | Varner et al. |
| 7,333,013 B2 | 2/2008 | Berger |
| 7,399,899 B2 | 7/2008 | Fabian |
| 7,446,646 B2 | 11/2008 | Huomo |
| 7,492,261 B2 | 2/2009 | Cambre et al. |
| 7,541,933 B2 | 6/2009 | Volpi et al. |
| 7,644,016 B2 | 1/2010 | Nycz et al. |
| 7,696,877 B2 | 4/2010 | Barnes et al. |
| 7,795,491 B2 | 9/2010 | Stewart et al. |
| 8,082,192 B2 | 12/2011 | Nycz et al. |
| 8,193,938 B2 | 6/2012 | Halberthal et al. |
| 8,256,674 B2 | 9/2012 | Fleck et al. |
| 8,371,448 B1 | 2/2013 | Reaux |
| 8,454,613 B2 | 6/2013 | Tethrake et al. |
| 8,477,076 B1 | 7/2013 | Nero, Jr. et al. |
| 8,479,989 B2 | 7/2013 | Fleck et al. |
| 8,872,662 B2 | 10/2014 | Halberthal et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,168,104 B2 | 10/2015 | Dein |
| 9,414,973 B2 | 8/2016 | Fleck et al. |
| 2002/0143320 A1 | 10/2002 | Levin |
| 2002/0188259 A1 | 12/2002 | Hickle et al. |
| 2003/0052788 A1 | 3/2003 | Kwong-Tai Chung |
| 2004/0129279 A1 | 7/2004 | Fabian et al. |
| 2005/0131397 A1 | 6/2005 | Levin |
| 2005/0203470 A1 | 9/2005 | Ballard |
| 2006/0047238 A1 | 3/2006 | Galdenzi et al. |
| 2006/0109086 A1 | 5/2006 | Amtmann |
| 2006/0187044 A1 | 8/2006 | Fabian et al. |
| 2006/0232407 A1 | 10/2006 | Ballard |
| 2009/0267765 A1 | 10/2009 | Greene et al. |
| 2010/0108079 A1 | 5/2010 | Blair |
| 2010/0109848 A1 | 5/2010 | Blair et al. |
| 2011/0004276 A1 | 1/2011 | Blair et al. |
| 2011/0181394 A1 | 7/2011 | Blair |
| 2014/0303606 A1* | 10/2014 | Garner-Richards ... A61B 19/44 606/1 |
| 2015/0054625 A1 | 2/2015 | Blair et al. |
| 2015/0115121 A1 | 4/2015 | Blair |
| 2015/0164603 A1 | 6/2015 | Fleck et al. |
| 2015/0216610 A1 | 8/2015 | Augustine |
| 2016/0157957 A1 | 6/2016 | Blair |
| 2016/0206399 A1 | 7/2016 | Blair |
| 2016/0210548 A1 | 7/2016 | Blair |
| 2016/0259954 A1 | 9/2016 | Buhler et al. |

FOREIGN PATENT DOCUMENTS

| | | |
|---|---|---|
| JP | 2009539478 A | 11/2009 |
| WO | 2007/146091 A1 | 12/2007 |
| WO | 2008/008449 A2 | 1/2008 |
| WO | 2008/024921 A1 | 2/2008 |
| WO | 2008/106552 A1 | 9/2008 |
| WO | 2008/133634 A1 | 11/2008 |
| WO | 2009/154987 A1 | 12/2009 |

OTHER PUBLICATIONS

Barnes et al., "Method, Apparatus and Article for Detection of Transponder Tagged Objects, for Example During Surgery," U.S. Appl. No. 61/091,667, filed Aug. 25, 2008, 76 pages.
Blair et al., "Improved Apparatus and Method for Detecting Objects Using Tags and Wideband Detection Device," U.S. Appl. No. 60/811,376, filed Jun. 6, 2006, 16 pages.
Blair et al., "Method and Apparatus to Detect Transponder Tagged Objects and to Communicate With Medical Telemetry Devices, for Example During Surgery," U.S. Appl. No. 61/222,847, filed Jul. 2, 2009, 122 pages.
Blair et al., "Method and Apparatus to Detect Transponder Tagged Objects and to Communicate With Medical Telemetry Devices, for Example During Medical Procedures," U.S. Appl. No. 61/242,699, filed Sep. 15, 2009, 158 pages.
Blair et al., "Method and Apparatus to Detect Transponder Tagged Objects, for Example During Medical Procedures," U.S. Appl. No. 61/242,704, filed Sep. 15, 2009, 127 pages.
Blair et al., "Method, Apparatus and Article for Detection of Transponder Tagged Objects, for Example During Surgery," U.S. Appl. No. 60/892,208, filed Feb. 28, 2007, 50 pages.
Blair et al., "Tag and Detection Device," U.S. Appl. No. 60/458,222, filed Mar. 27, 2003, 23 pages.
Blair, "Detectable Surgical Objects and Methods of Making Same," U.S. Appl. No. 61/109,142, filed Oct. 28, 2008, 47 pages.
Blair, "Method and Apparatus to Account for Transponder Tagged Objects Used During Medical Procedures," U.S. Appl. No. 61/263,726, filed Nov. 23, 2009, 78 pages.
Blair, "Transponder Device to Mark Implements, Such as Surgical Implements, and Method of Manufacturing and Using Same," U.S. Appl. No. 61/086,727, filed Aug. 6, 2008, 30 pages.
Blair, "Transponder Device to Mark Implements, Such as Surgical Implements, and Method of Manufacturing and Using Same," U.S. Appl. No. 61/220,452, filed Jun. 25, 2009, 46 pages.
Blair, "Transponder Device to Mark Implements, Such as Surgical Implements, and Method of Manufacturing and Using Same," U.S. Appl. No. 61/224,323, filed Jul. 9, 2009, 57 pages.
Macario et al., "Initial Clinical Evaluation of a Handheld Device for Detecting Retained Surgical Gauze Sponges Using Radiofrequency Identification Technology," Arch Surg 141:659-662, Jul. 2006.
Black, "Method and Apparatus to Account for Transponder Tagged Objects During Clinical Procedures, Employing a Trocar," U.S. Appl. No. 62/360,869, filed Jul. 11, 2016, 99 pages.
Black, "Method and Apparatus to Account for Transponder Tagged Objects Used During Clinical Procedures, Employing a Trocar," U.S. Appl. No. 62/378,515, filed Aug. 23, 2016, 103 pages.
Haldor Advanced Technologies, "Haldor Advanced Technologies Releases a Breakthrough New Sponge Management Solution: Modular, Mobile, Wireless, and Tailored per Use-case and Requirements," Sep. 8, 2015, retrieved from http://wwl.prweb.com/prifiles/2015/09/06/12938762/ORLocate%205Sponge%20Solution-September%202015.pdf, 2 pages.
Hansen et al., "Method and Apparatus to Account for Transponder Tagged Objects Used During Clinical Procedures, Employing a Shielded Receptacle," U.S. Appl. No. 62/360,864, filed Jul. 11, 2016, 99 pages.
Hansen et al., "Method and Apparatus to Account for Transponder Tagged Objects Used During Clinical Procedures Employing a Shielded Receptacle With Antenna," U.S. Appl. No. 62/360,866, filed Jul. 11, 2016, 154 pages.
Poirier et al., "Method and Apparatus to Account for Transponder Tagged Objects Used During Clinical Procedures, for Example Including Count in and/or Count Out and Presence Detection," U.S. Appl. No. 62/360,868, filed Jul. 11, 2016, 113 pages.
Poirier et al., "Method and Apparatus to Account for Transponder Tagged Objects Used During Clinical Procedures, for Example Including Count in and/or Count Out and Presence Detection," U.S. Appl. No. 62/378,511, filed Aug. 23, 2016, 114 pages.
International Search Report and Written Opinion dated Feb. 4, 2015, for corresponding International Application No. PCT/US2014/062152, 9 pages.

* cited by examiner

SURGICAL SPONGE DISTRIBUTION SYSTEMS AND METHODS

BACKGROUND

Technical Field

The present disclosure generally relates to surgical sponges, and more particularly to systems and methods useful in counting surgical sponges used during surgical procedures.

Description of the Related Art

Absorbent devices such as surgical sponges or gauze pads absorb bodily fluids during surgical procedures. Surgeons or other care providers may pack sponges in various bodily cavities. Often the sponges are wadded up when packed into the bodily cavities. Once saturated with bodily fluids, sponges are difficult to locate and extract from a patient prior to closing or completing the surgical procedure. Retained sponges, accidentally left inside of a patient post-surgery can cause infections and hinder patient recovery. Retained sponges may even require an additional surgical procedure to retrieve the retained surgical sponge. Reducing the occurrence of retained objects is a primary concern of surgical facilities.

Most medical facilities have implemented counting procedures or protocols to be used during each surgical procedure. Typically, a count of all objects available for use during a medical procedure is performed before the start of the medical procedure. The objects may include surgical sponges or lap sponges. Alternatively, the surgical or lap sponges may be counted separately from, for example surgical implements. At the end of a medical procedure, for example prior to closing of a surgical wound or opening, a count is performed of all objects either unused or retrieved from the body. The ending counting is compared to the starting count to determine if there is a discrepancy. If no discrepancy is found, the medical care provider may close the surgical wound. Otherwise, a search is performed to locate the missing object(s). These protocol reduce the likelihood of accidentally allowing a sponge to remain in a patient at the conclusion of a surgical procedure.

BRIEF SUMMARY

Given the abundant use of surgical sponges including lap sponges or gauze during medical procedures, for instance surgery or labor and delivery procedures, surgical sponges are challenging to track to prevent unintended retention during medical procedures. Maintaining an accurate count of the number of surgical sponges used in a medical procedure is often an integral part of ensuring no surgical sponges remain in a patient at the conclusion of the medical procedure. Such sponge counts rely upon an accurate determination of the number of sponges used between the start of the procedure and the time of the sponge count. Described herein are new, non-obvious, surgical sponge dispensing systems that readily permit a fast and accurate accounting of the number of sponges dispensed during a procedure.

An elongated flexible strip of material may carry a plurality of surgical sponges. One or more fasteners (e.g., snaps, hook and loop fastener, buttons, clips), stitches, threaded loops or one or more knotted threaded loops can attach each of the surgical sponges to the elongated flexible strip of material. Alternatively, the surgical sponges may be integral, yet severable form, the elongated flexible strip of material, for instance via perforations or slits. The elongated flexible strip of material can include a unitary strip made from any type of severable material or may include a number of individual strips serially attached to each other, with each of the individual strips having a fixed number of surgical sponges attached thereto. The elongated flexible strips of material may include, a lint free material or a polymeric material able to be cut to any desired like prior to or during a surgical procedure. The one or more fasteners coupling each surgical sponge to the elongated flexible strip of material may have a construction that facilitates the separation of the surgical sponge from the elongated flexible strip without the use of an instrument, such as a knife or scissors.

The elongated flexible strip of material may include demarcations or other markings. Such markings may, for example be placed at intervals between which are attached a defined or known number of surgical sponges (every 3 sponges, every 5 sponges, etc.). Such markings may, for example be placed at defined length intervals (every 6 inches, every 12 inches, etc.) and the surgical sponges attached at a regular density (2 sponges every 6 inches, 4 sponges every 12 inches, etc.). During a medical procedure, the medical staff determines the number of surgical sponges used to that point in the medical procedure by examining the elongated flexible strip of material and performing a simple calculation based upon the length of elongated flexible strip of material from which surgical sponges have been detached. Based on the known number of surgical sponges for the given length of elongated flexible strip of material, the number of sponges used to that point in the medical procedure is determined.

In another instance, each sponge attached to the elongated flexible strip of material may be associated with and/or have a 1:1 correspondence to an alphanumeric identifier (e.g., serial number) carried the elongated flexible strip of material. In such an implementation, the number of surgical sponges used in a procedure may be readily and accurately determined by examining the alphanumeric identifiers on the elongated flexible strip of material.

In at least some instances, such unique alphanumeric identifiers may include one or more radio frequency identification devices carried by each surgical sponge and the elongated flexible member. In such instances, scanning or interrogating the elongated flexible member provides a count of the number of surgical sponges used to that point in the procedure.

An article for use in medical procedures may be summarized as including an elongated flexible strip of material having a first end and a second end; and a plurality of surgical sponges physically separately coupled to the elongated flexible strip of material at respective fixed locations spaced along the elongated flexible strip of material, each of the surgical sponges individually physically detachable from the article. Detachment of any outermost one of the surgical sponges from the article may not cause detachment of any of the other surgical sponges of the plurality of surgical sponges from the article. The surgical sponges may each be individually physically detachable from the elongated flexible strip of material. The surgical sponges may each be individually physically detachable from the elongated flexible strip of material without severing the elongated flexible strip of material. The surgical sponges may each be individually stitched to the elongated flexible strip of material at the respective fixed locations spaced along the elongated flexible strip of material. The surgical sponges may each be individually stitched along a portion of a respective single edge thereof to the elongated flexible strip of material at the respective fixed locations via at least one thread that is severable at a lower force than that required to sever the elongated flexible strip of material. The surgical sponges may each be individually stitched along all of a respective single edge thereof to the elongated flexible strip of material at the respective fixed locations via at least one thread that is severable at a lower force than that required to sever the elongated flexible strip of material. The surgical sponges may each be individually fixed to the elongated flexible strip of material at the respective fixed locations spaced along the elongated flexible strip of material via a plurality of serviceable knots. The surgical sponges may each be individually fixed to the elongated flexible strip of material at the respective fixed locations spaced along the elongated flexible strip of material via a plurality of serviceable knots tied in the elongated flexible strip of material. The surgical sponges may each be individually fixed to the elongated flexible strip of material at the respective fixed locations spaced along the elongated flexible strip of material via a plurality of fasteners. The elongated flexible strip of material may include a woven textile. The woven textile may include a woven low- or lint-free textile. The elongated flexible strip of material may include a non-woven polymer material. The surgical sponges may be spaced at a fixed interval from one another along the elongated flexible strip of material. In addition to being detachably attached to the elongated flexible strip of material, adjacent ones of the surgical sponges may be detachably attached to one another and arranged in an accordion pattern. The surgical sponges may each bear a respective indicia, the respective indicia identifying a position of the respective surgical sponge in an ordered sequence along the elongated flexible strip of material. The elongated flexible strip of material may include a plurality of demarcations therealong, the demarcations corresponding to respective ones of the surgical sponges or respective ones of locations of the respective surgical sponges along the elongated flexible strip of material.

A medical device inventory management method may be summarized as including determining at a first time a first number of surgical sponges coupled to an article for use in a medical procedure, the article for use in medical procedures including: an elongated flexible strip of material having a first end and a second end; and a plurality of surgical sponges physically separately coupled to the elongated flexible strip of material at respective fixed locations spaced along the elongated flexible strip of material, each of the surgical sponges individually physically detachable from the article; determining at a second time, subsequent to the first time, a second number of surgical sponges coupled to the article for use in the medical procedure; and determining the number of surgical sponges removed from the article for use in the medical procedure between the first time and the second time. Determining at a first time a first number of surgical sponges coupled to an article for use in a medical procedure may include determining the first number of surgical sponges coupled to the article using at least one of: a demarcation carried by the elongated flexible strip of material, a demarcation carried by at least a portion of the plurality of surgical sponges, or a demarcation carried by at least a portion of the plurality of surgical sponges and the elongated flexible strip of material. Determining at a second time a second number of surgical sponges coupled to an article for use in a medical procedure may include determining the second number of surgical sponges coupled to the article using at least one of: a demarcation carried by the elongated flexible strip of material, a demarcation carried by at least a portion of the plurality of surgical sponges, or a demarcation carried by at least a portion of the plurality of surgical sponges and the elongated flexible strip of material.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. For example, details regarding surgical sponges and similar surgical devices and/or implements have not been shown or described in detail to avoid unnecessarily obscuring descriptions of the embodiments. Similarly, the operating room environment and similar medical environments are not discussed in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense that is as "including, but not limited to."

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings and Abstract of the Disclosure provided herein are for convenience only and do not interpret the scope or meaning of the embodiments.

Figure 1A:
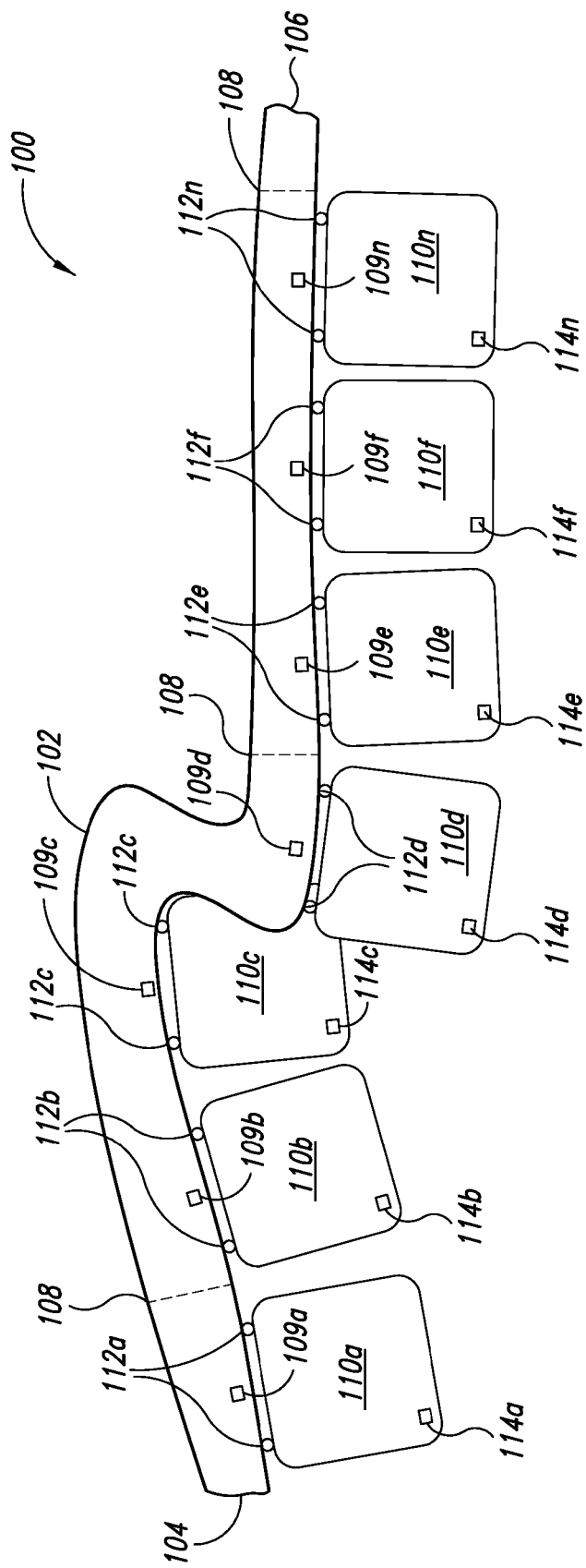
FIGS. 1A and 1B are elevation views of an illustrative surgical sponge distribution system including an elongated flexible strip of material having attached at fixed locations thereto a plurality of surgical sponges, according to one non-limiting illustrated embodiment.
Figure 1B:
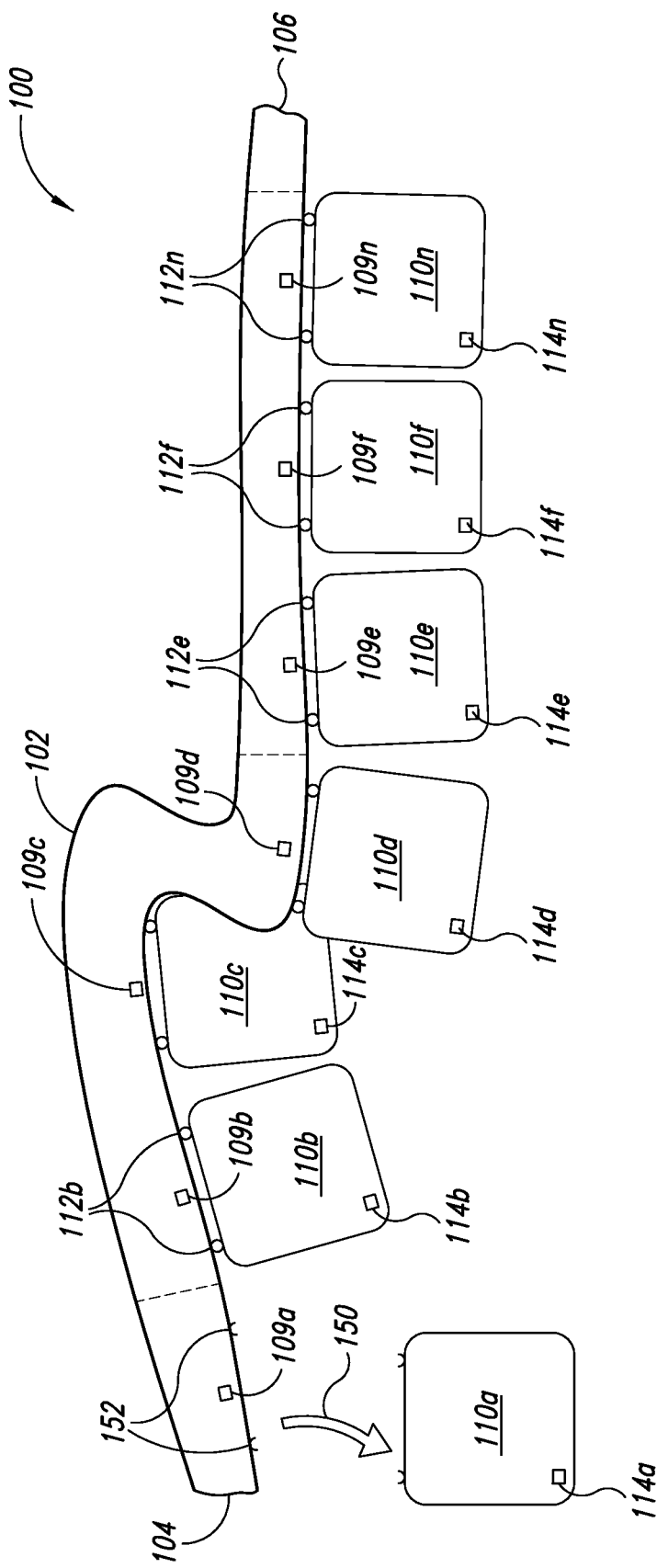

FIGS. 1A and 1B show an illustrative system 100 that includes an elongated flexible strip of material 102 to which a plurality of surgical sponges 110*a*-110*n* (collectively "surgical sponges 110," singly "sponge 110") are attached at respective fixed locations. Fasteners 112*a*-112*n* (collectively "fasteners 112," singly "fastener 112") attach each respective surgical sponge 110*a*-110*n* to the elongated flexible strip of material 102 at fixed locations. FIG. 1A shows an illustrative system 100 that includes an elongated flexible strip of material 102 having a plurality of surgical sponges 110 attached at fixed locations. FIG. 1B shows the illustrative system 100 after detaching 150 a surgical sponge 110*a* from the first fixed location by breaking or otherwise disrupting the fasteners 112*a* attaching the surgical sponge to the flexible strip of material 102.

In some instances, the elongated strip of flexible material 102 may carry demarcations 108. In some implementations, such demarcations 108 may be spaced after a fixed number of surgical sponges (every 2 sponges, every 5 sponges, every 10 sponges, etc.) to permit the rapid determination of the number of sponges detached or removed from the elongated flexible strip of material 102. In some implementations, such demarcations 108 may be spaced at a fixed distance (every 3 inches, every 6 inches, every 12 inches, etc.) to permit the rapid determination of the number of sponges detached removed from the elongated flexible strip of material 102. In such instances, a known number of surgical sponges may be attached at fixed locations in a given length of elongated flexible strip of material 102 (e.g., 3 sponges every 6 inches, 8 sponges every 12 inches). Demarcations may be visually indicated by visually recognizable indicia, for instances number or letters, or colors.

In yet other instances, the elongated strip of flexible material 102 may carry alphanumeric identifiers 109*a*-109*n* (collectively "alphanumeric identifiers 109," singly "alphanumeric identifier 109") corresponding to the alphanumeric identifier 114*a*-114*n* (collectively "alphanumeric identifier 114," singly "alphanumeric identifier 114") carried by a surgical sponge proximate the location of the alphanumeric identifier 109 on the elongated trip of flexible material 102. In such instances, the alphanumeric identifiers on the elongated flexible strip of material 102 permit the rapid determination of the number of sponges detached or removed from the elongated flexible strip of material 102.

The elongated flexible strip of material 102 may include any material or substance to which the plurality surgical sponges 110 are attached or physically coupled. For instance, the surgical sponges 110 are attached or physically coupled to the elongated flexible strip of material 102 via one or more fasteners 112, including stitches. Alternatively, the surgical sponges 110 are integrally formed with the elongated flexible strip of material 102, and are selectively separable therefrom, for instance via perforations or scoring. In at least some instances, the elongated strip of flexible material 102 is a woven textile. In at least some instances, the elongated flexible strip of material 102 is a woven low lint or lint free textile. In other instances, the elongated flexible strip of material 102 is a non-woven polymeric material.

The elongated flexible strip of material 102 can be of any length and includes at least a first end 104 and a second end 106. In some instances, the first end 104 and the second at 106 may include the entirety of the elongated flexible strip of material 102. In other instances, first at 104 and the second at 106 may include only a portion of the entirety of the elongated flexible strip of material 102. For example, when the elongated strip of flexible material 102 is severed (e.g., cut, ripped, torn, otherwise separated) any number of portions of elongated strips of flexible material 102 may be formed, each of the portions having a first at 104 and a second at 106. In at least some instances, the elongated strip of flexible material 102 may include a single strip of flexible material extending continuously from the first and 104 to the second end 106. In other instances the elongated strip of flexible material 102 may include any number of separable segments each segment having a respective first end 104 and second and 106. The separable segments physically coupled using one or more fasteners (e.g., clips, snaps, stitches, knots) to provide a single, though separable or severable, elongated strip of flexible material 102.

Using the demarcations 108 or the alphanumeric identifiers 109, and/or distinctive variety of colors the number of surgical sponges included in any length of elongated flexible strip of material 102 may be readily determined. For example, if the elongated strip of flexible material 102 carries six surgical sponges 110 per foot, and demarcations 108 are provided every 6 inches of elongated strip of flexible material one may readily determine that a 6½ foot length of elongated strip of flexible material carrying thirteen demarcations 108 once carried thirty-nine (39) surgical sponges 110. In another example, if the elongated strip of flexible material 102 carries alphanumeric identifiers 109 in the form of a serial number corresponding to each attached surgical sponge 110, medical personnel may readily determine the number of surgical sponges 110 removed from the elongated flexible strip of material 102 by simply subtracting the beginning and ending serial numbers.

One or more attachment devices detachably attach or detachably physically couple each of the surgical or lap sponges 110 to the elongated strip of flexible material 102. In some instances, the attachment devices include one or more fasteners 112 that physically attach or couple each of the surgical sponges 110 to the elongated flexible strip of material 102. Such fasteners 112 may include any device, system, or combination of systems and devices capable of providing a physical coupling between the surgical sponges 110 and the elongated flexible strip of material 102. Examples of such fasteners 112 include, but are not limited to, hook-and-loop fasteners, snap fasteners, button fasteners, clips, and similar.

In other instances, the attachment devices include one or more stiches or threaded loops that physically attach or couple each of the surgical or lap sponges 110 to the elongated flexible strip of material 102. Such stitches or threaded loops include woven or monofilament threaded knotted loops, tied loops, bonded loops, or the like. In at least some instances, the threaded loops can include one or more removable knots such as one or more serviceable knots. The stitches or threaded loops can include any material capable of permitting detachment of the surgical sponge 110 from the elongated flexible strip of material 102. For example, the stitches or threaded loops may include a rupturable, fracturable, or disruptable polymeric or elastomeric material. In at least some instances, medical personnel may apply such a force by simply pulling the surgical sponge 110 from the elongated strip of flexible material 102. Such an attachment method advantageously beneficially permits ready access to any number of surgical sponges 110 by medical personnel without requiring the use of a sharp instrument or other tool to separate the surgical or lap sponge 110 from elongated strip flexible material 102. In some instances, the surgical sponges 110 maybe each individually stitched to the elongated strip of flexible material 102 via stitches or threaded loops that are severable at a lower force than that required to sever the elongated flexible strip material 102.

In yet other instances, the attachment devices include one or more perforations between the surgical or lap sponge 110 and the elongated flexible strip of material 102. Such perforations or the like permit the detachment of the surgical sponge 110 from an at least partially integrally formed portion of the elongated flexible strip of material 102. Such a perforated construction provides a weak seam between the surgical sponge 110 and the elongated flexible strip of material 102. Upon application of tensile force to the surgical sponge (e.g., pulling by personnel), the surgical sponge 110 tears away from the elongated flexible strip of material 102 at the weak seam provided by the perforations.

Importantly, regardless of the method of physical attachment between the surgical sponge 110 and the elongated flexible strip of material 102, detachment of the surgical sponge 110 from the elongated strip of flexible material 102 occurs without physical damage occurring to the surgical sponge 110 or the elongated strip of flexible material 102. By preventing damage to the surgical sponge 110 the utility in physical integrity of the surgical sponge 110 is maintained. By preventing damage to the elongated strip of flexible material 102 and accurate and reliable inventory of surgical sponges 110 is possible.

Figure 2A:
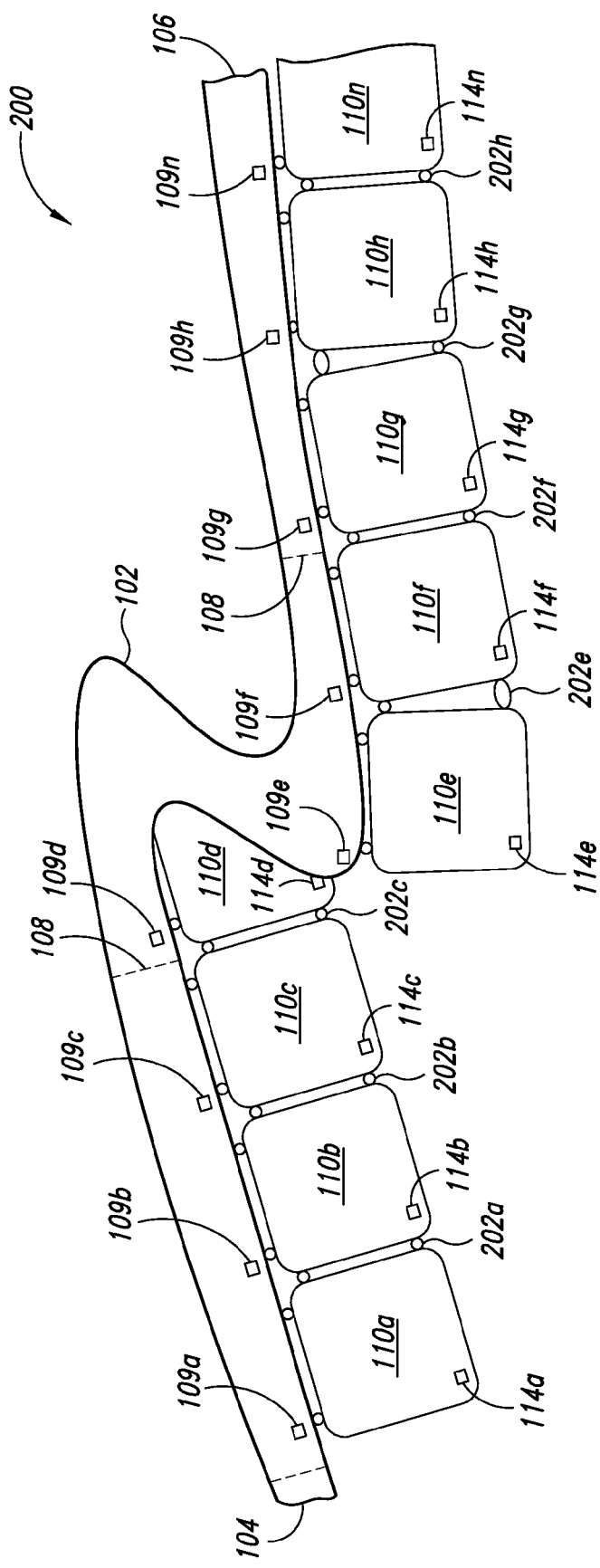
FIGS. 2A and 2B are elevation views of an illustrative surgical sponge distribution system including an elongated flexible strip of material having attached at fixed locations thereto a plurality of surgical sponges which are also attached to at least one other surgical sponge, according to one non-limiting illustrated embodiment.
Figure 2B:
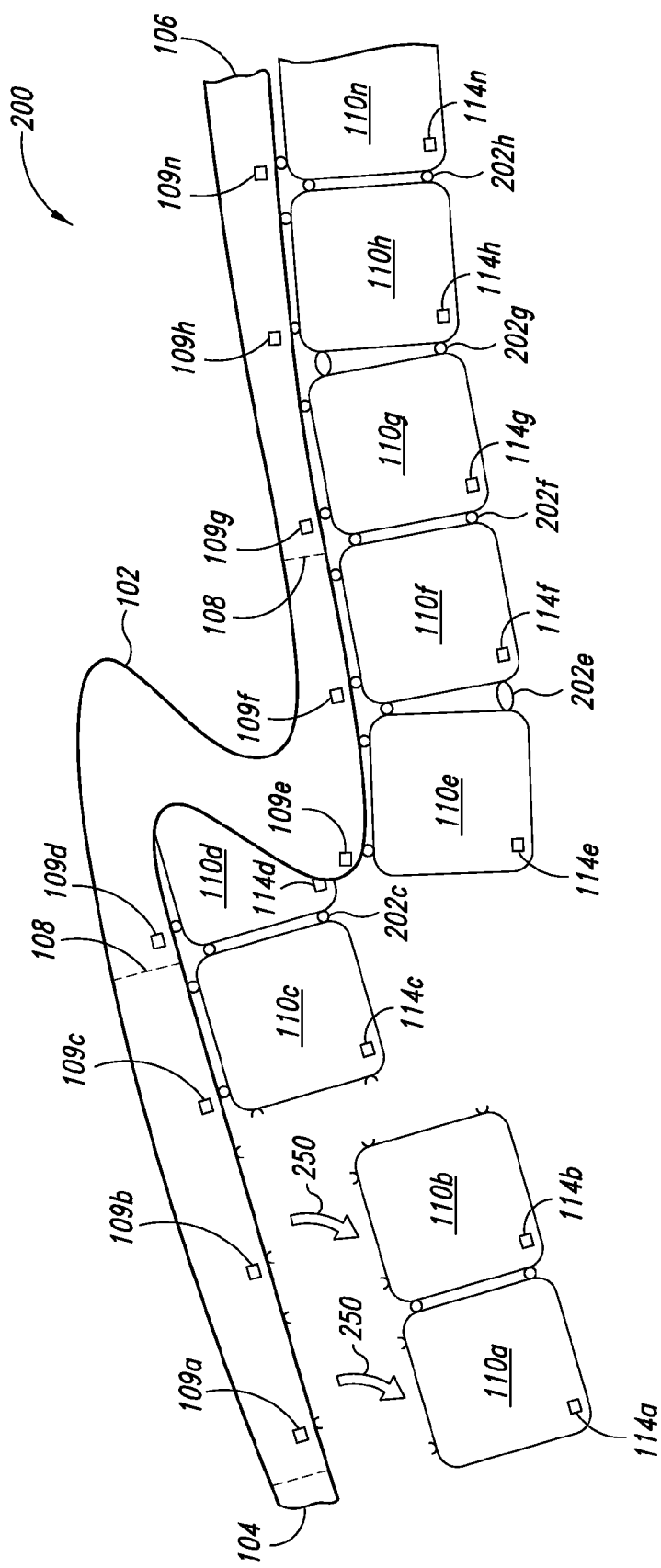

FIGS. 2A and 2B show an illustrative system 200 that includes an elongated flexible strip of material 102 to which a plurality of surgical sponges 110a-110n (collectively "surgical sponges 110," singly "sponge 110") are attached at respective fixed locations. Attachment devices attach each respective surgical sponge 110a-110n to the elongated flexible strip of material 102 at fixed locations. Attachment devices 202a-202n (collectively "attachment devices 202," singly "attachment device 202") attach each surgical sponge 110 to at least one neighboring surgical sponge 110. FIG. 2A shows an illustrative system 200 that includes an elongated flexible strip of material 102 having a plurality of surgical or lap sponges 110 attached at fixed locations. FIG. 2B shows the illustrative system 200 after detaching 250 two surgical sponges 110a and 110b from the elongated flexible strip of material 102 by disengaging, fracturing, breaking, or otherwise disrupting the attachment devices. Attachment device 202a couples the detached surgical sponges 110a and 110b to each other.

One or more attachment devices 202 detachably attach or detachably physically couple each of the surgical sponges 110 to at least one other neighboring surgical sponge 110. In some instances, the attachment devices 202 include one or more fasteners that physically attach or couple each of the surgical sponges 110 to at least one other surgical sponge 110. Such fasteners may include any device, system, or combination of systems and devices capable of providing a physical coupling between each of the surgical sponges 110 and at least one other surgical sponge 110. Examples of such fasteners include, but are not limited to, hook-and-loop fasteners, snap fasteners, button fasteners, clips, and similar.

In other instances, the attachment devices 202 include one or more stiches or threaded loops that physically attach or couple each of the surgical or lap sponges 110 to at least one other neighboring surgical sponge 110. Such stitches or threaded loops include woven or monofilament threaded knotted loops, tied loops, bonded loops, or the like. In at least some instances, the threaded loops can include one or more removable knots such as one or more serviceable knots. The stitches or threaded loops can include any material capable of permitting detachment of the surgical sponge 110 from the at least one neighboring surgical sponge 110. For example, the stitches or threaded loops may include a rupturable, fracturable, or disruptable polymeric or elastomeric material. In at least some instances, medical personnel may apply such a force by simply pulling the surgical sponge 110. Such an attachment method advantageously beneficially permits ready access to any number of surgical sponges 110 by medical personnel without requiring the use of a sharp instrument or other tool to separate one or more attached surgical lap sponges 110 from the one or more neighboring surgical sponges 110.

In yet other instances, the attachment devices 202 may include a number of perforations separating each of the surgical sponges 110 from at least one other neighboring surgical sponge 110. Such perforations or similar structurally weakened joints or seams between integrally formed, neighboring, surgical sponges 110 permit the detachment of one or more surgical sponges 110 from at least one neighboring surgical sponge 110.

Importantly, regardless of the method of physical attachment between the surgical sponges 110, detachment of one or more surgical sponges 110 from the elongated flexible strip of material 102 and one or more neighboring surgical sponges 110 occurs without physical damage occurring to the surgical sponge 110, the elongated strip of flexible material 102 or the one or more neighboring surgical sponges 110. By preventing damage to the surgical sponge 110 and the one or more neighboring surgical sponges 110, the utility and physical integrity of all of the surgical sponges 110 is maintained. By preventing damage to the elongated strip of flexible material 102 and accurate and reliable inventory of surgical sponges 110 is possible.

Figure 3:
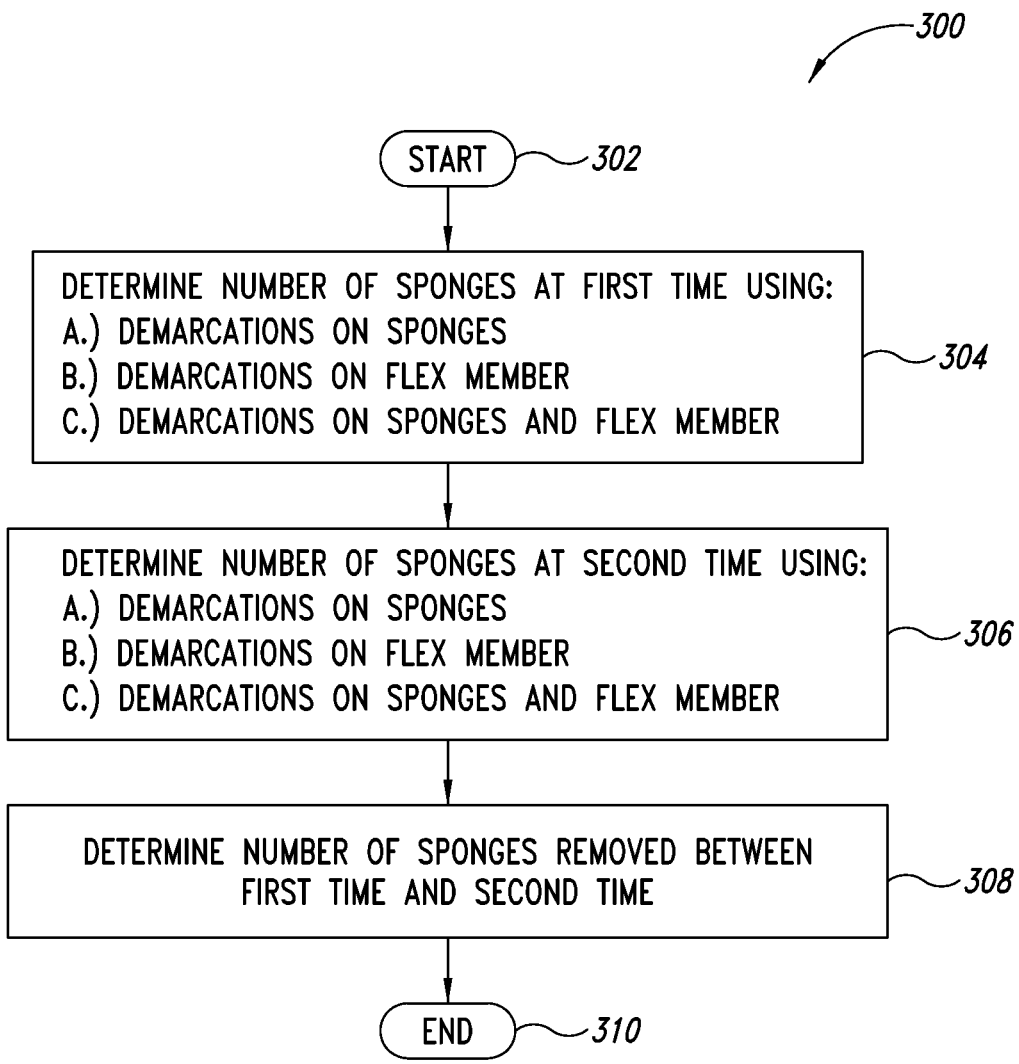
FIG. 3 is a high-level logic flow diagram of an illustrative method for performing a sponge count during a medical procedure when using a surgical sponge distribution system such as the sponge distribution system depicted in FIG. 1A or 2A, according to one non-limiting illustrated embodiment.

FIG. 3 shows an illustrative high-level method 300 of determining a number of sponges used during a procedure using a surgical sponge distribution system 100 such as that depicted in FIGS. 1A and 1B or a surgical sponge distribution system 200 such as that depicted in FIGS. 2A and 2B. A surgical sponge distribution system 100, 200 may be used in a surgical or similar medical environment. In some instances, the surgical sponge distribution system 100, 200 may be provided in a container or similar portable structure to facilitate positioning in a location convenient for access and delivery of the surgical sponges 110. At During a procedure personnel may detach surgical sponges 110 as needed from the elongated flexible strip of material 102. At the conclusion of the procedure, the attending personnel determine the number of sponges consumed using the demarcations 108 and/or alphanumeric identifiers 109 carried by the elongated flexible strip of material 102. The method 300 of determining the number of sponges used during a procedure commences at 302.

At 304, the location of the first surgical sponge 110 attached to the elongated flexible strip of material 102 is determined. In some instances, personnel identify the first surgical sponge 110 using demarcations 108 printed on or otherwise affixed to the elongated flexible strip of material 102. In other instances, personnel identify the first surgical sponge 110 using alphanumeric identifiers 109 printed on or otherwise affixed to the elongated strip of material 102. In yet other instances, personnel identify the first surgical sponge 110 by reading or otherwise interrogating radio frequency identification tags carried by the elongated flexible strip of material 102, by some or all of the surgical sponges 110a-110n, or by both the elongated flexible strip of material 102 and the surgical sponges 110a-110n. In some instances, personnel manually record the location and/or identity of the first surgical sponge 110. In some instances, personnel enter the location and/or identity of the first surgical sponge 110 in a surgical item inventory control system. In yet other instances, a surgical item inventory control system autonomously determines (e.g., using RFID technology) the location and/or identity of the first surgical sponge 110.

At 306, the location of the last surgical sponge 110 removed from the elongated flexible strip of material 102 is determined. In some instances, personnel identify the last removed surgical sponge 110 using demarcations 108 printed on or otherwise affixed to the elongated flexible strip of material 102. In other instances, personnel identify the last removed surgical sponge 110 using alphanumeric identifiers 109 printed on or otherwise affixed to the elongated strip of material 102. In yet other instances, personnel identify the last removed surgical sponge 110 by reading or otherwise interrogating radio frequency identification tags carried by the elongated flexible strip of material 102, by some or all of the surgical sponges 110a-110n, or by both the elongated flexible strip of material 102 and the surgical sponges 110a-110n. In some instances, personnel manually record the location and/or identity of the last removed surgical sponge 110. In some instances, personnel enter the location and/or identity of the last removed surgical sponge 110 in a surgical item inventory control system. In yet other instances, a surgical item inventory control system autonomously determines (e.g., using RFID technology) the location and/or identity of the last removed surgical sponge 110.

At 308, the number of surgical sponges removed from the elongated flexible strip of material 102 is determined. In at least some implementations, personnel determine the number of surgical sponges removed using the location information of the first sponge determined at 304 and the location information of the last removed sponge determined at 306. For example, if the elongated flexible strip of material 102 includes demarcations every 5 sponges and two full demarcations exist between the first sponge and the last sponge removed, it can be quickly determined that 10 sponges have been removed and used in the procedure. In another example, the elongated flexible strip of material 102 includes alphanumeric identifiers 109 in the form of serial numbers having a 1:1 correspondence with the attached surgical sponges 110. By determining the serial numbers corresponding to the first sponge and the last removed sponges, the number of sponges removed during the procedure can be determined. Although the provided examples are not exhaustive, one of ordinary skill in the art can readily appreciate the number and variety of sponge count determination methods possible using the surgical sponge distribution system 100, 200. The method 300 of determining the number of sponges used during a procedure concludes at 310.

Figure 4:
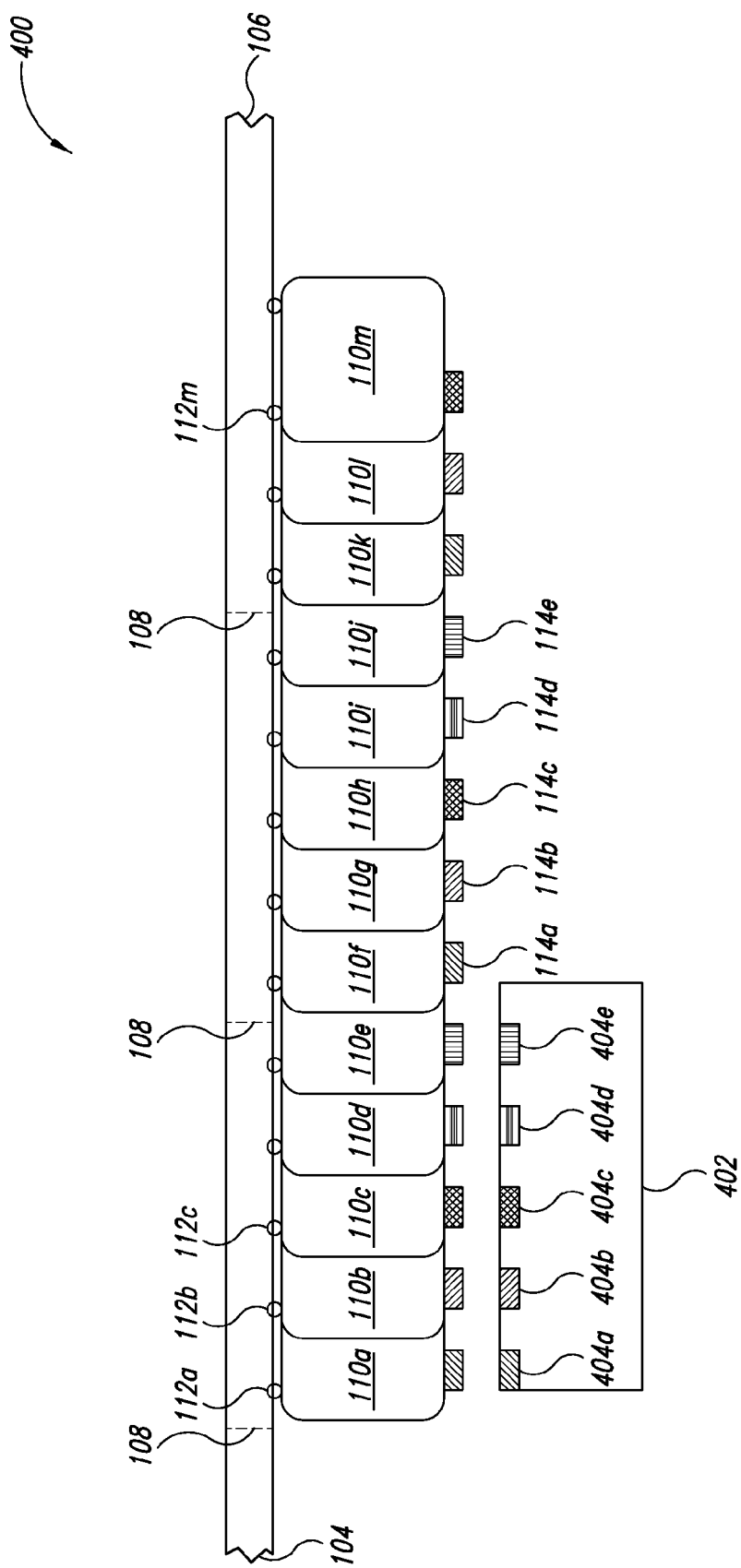
FIG. 4 is an elevation view of an illustrative surgical sponge distribution system including an elongated flexible strip of material having attached at fixed locations thereto a plurality of surgical sponges each of which is identifiable by an attached tag having a defined pattern and/or color, according to one non-limiting illustrated embodiment.

FIG. 4 shows an illustrative system 400 that includes an elongated flexible strip of material 102 to which a plurality of surgical sponges 110a-110m (collectively "surgical sponges 110;" singly, "surgical sponge 110") are attached at respective fixed locations. Each surgical sponge 110a-110m attaches to the elongated strip of flexible material 102 at a fixed location along the elongated flexible strip of material 102. In some implementations, the elongated strip of flexible material 102 contains demarcations 108 that may include printed characters, perforations, or the like. The demarcations 108 may be spaced at regular intervals along the elongated strip of flexible material 102.

As depicted in FIG. 4, each surgical sponge 110a-110m carries a respective tag 114a-114e. The tags 114a-114e attach to the surgical sponges 110 in a defined, recurring, sequence. A defined, recurring, sequence may include any number of tags, such as the recurring five-tag sequence 114a-114e depicted in FIG. 4. Each of the tags 114 in a sequence carries at least one identifying characteristic that uniquely distinguishes the tag 114 (e.g., tag 114a) from at least all of the other tags in the same sequence (e.g., tags 114b-114e). In some instances, the tags 114a-114e may have a recurring defined color sequence, such as a five-color repeating sequence of: red, yellow, blue, orange, and green. In other instances, the tags 114a-114e may carry a different identifier symbol such as a geometric shape (e.g., circle, square, triangle), letter, number or the like. In other instances, the tags 114a-114e may carry a recurring sequence of different physical identifier symbols such as braille characters corresponding to the numbers 1, 2, 3, and so on. In at least some instances, the demarcations 108 align with a defined point in the recurring tag sequence, for example, the demarcations 108 may occur after the last tag 114 occurring in a series (e.g., after tag 114e in FIG. 4) or prior to the first tag 114 occurring in a series (e.g., prior to tag 114a in FIG. 4).

A reference card 402 bearing indicia 404a-404e corresponding to each of the patterns or colors of the respective tags 114a-114e can be used in conjunction with the demarcations 108 to determine the number of surgical sponges 110 removed from the elongated strip of flexible material 102. For example, the number of surgical sponges used may be determined by counting the number of demarcated empty elongated strip of flexible material 102 sections and adding to this total the number of surgical sponges removed from the first full or partial surgical sponge sequence. Thus, an elongated strip of flexible material 102 having three empty demarcated five-sponge groups and a fourth group having two sponges removed as determined using a five-tag reference card 402, indicates the removal of seventeen surgical sponges 110 from the elongated strip of flexible material 102.

The various methods may include additional acts, omit some acts, and may perform the acts in a different order than set out in the various flow diagrams. The use of ordinals such as first, second and third, do not necessarily imply a ranked sense of order, but rather may only distinguish between multiple instances of an act or structure.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to: Provisional U.S. Patent Application Ser. No. 61/895,034 filed Oct. 24, 2013, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An article for use in medical procedures, the article comprising:
an elongated flexible strip of material having a first end and a second end; and
a plurality of surgical sponges physically separately coupled to the elongated flexible strip of material at respective fixed locations spaced along the elongated flexible strip of material, each of the surgical sponges individually physically detachable from the article, each of the surgical sponges individually stitched along a portion of a respective single edge thereof to the elongated flexible strip of material at the respective fixed locations via at least one thread that is severable at a lower force than that required to sever the elongated flexible strip of material.

2. The article of claim 1 wherein detachment of any outermost one of the surgical sponges from the article does not cause detachment of any of the other surgical sponges of the plurality of surgical sponges from the article.

3. The article of claim 1 wherein the surgical sponges are each individually physically detachable from the elongated flexible strip of material.

4. The article of claim 1 wherein the surgical sponges are each individually physically detachable from the elongated flexible strip of material without severing the elongated flexible strip of material.

5. The article of claim 1 wherein the surgical sponges are each individually stitched to the elongated flexible strip of material at the respective fixed locations spaced along the elongated flexible strip of material.

6. The article of claim 1 wherein the surgical sponges are each individually stitched along all of a respective single edge thereof to the elongated flexible strip of material at the respective fixed locations via at least one thread that is severable at a lower force than that required to sever the elongated flexible strip of material.

7. The article of claim 1 wherein the elongated flexible strip of material comprises a woven textile.

8. The article of claim 7 wherein the woven textile comprises a woven low- or lint-free textile.

9. The article of claim 1 wherein the elongated flexible strip of material comprises a non-woven polymer material.

10. The article of claim 1 wherein the surgical sponges are spaced at a fixed interval from one another along the elongated flexible strip of material.

11. The article of claim 1 wherein in addition to being detachably attached to the elongated flexible strip of material, adjacent ones of the surgical sponges are detachably attached to one another and arranged in an accordion pattern.

12. The article of claim 1 wherein the surgical sponges each bear a respective indicia, the respective indicia which identifies a position of the respective surgical sponge in an ordered sequence along the elongated flexible strip of material.

13. The article of claim 1 wherein the elongated flexible strip of material includes a plurality of demarcations therealong, the demarcations which correspond to one or more respective surgical sponges or one or more respective locations of the respective surgical sponges along the elongated flexible strip of material.

* * * * *